United States Patent [19]

Sarneel

[11] Patent Number: Plant 5,464

[45] Date of Patent: May 7, 1985

[54] CARNATION NAMED MEDEA

[75] Inventor: J. F. Sarneel, Nieuwveen, Netherlands

[73] Assignee: Milek en Zonen B.V., Nieuwveen, Netherlands

[21] Appl. No.: 508,863

[22] Filed: Jun. 29, 1983

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Chas. W. Rummler

[57] ABSTRACT

A new and distinct variety of carnation plant characterized by its continuous and profuse production of very light orange, or peach colored, blossoms of medium size, its tall and vigorous growth habit with strong stem character, and by its abundant production of foliage and its alternate branching character.

1 Drawing Figure

BACKGROUND OF THE NEW PLANT

My new carnation cultivar originated as a seedling of unknown parentage growing in a field of seedlings hybridized by crossing other unidentified carnation plants selected by me from a field of carnation plants maintained in greenhouse at Nieuwveen, Holland, for breeding purposes. My purpose in this hybridizing was to find new varieties of carnations having improved production characteristics and quality of color. This plant was selected by me for propagation and test because of its light peach coloration which, at the tips, is almost white and occasionally having rather short, bright red marginal stripes at the tips of the larger outer petals. I reproduced this parent plant by means of cuttings at Nieuwveen, Holland, to observe its ability to reproduce the characteristics noted in the parent plant and finding this to be successful, I continued such propagation through several successive generations and determined conclusively that the distinctive characteristics of the plant held true from generation to generation and appeared to be firmly fixed.

This new variety of carnation is now being propagated on a commercial scale at Nieuwveen, Holland, and at Wheat Ridge, Col., U.S.A.

DESCRIPTION OF THE DRAWINGS

My new variety of carnation plant is illustrated by the accompanying photographic drawings which show, in full color, typical buds at various stages of opening, as well as fully opened flowers in the lower view, and in the upper view, a three-quarter face view of one of the flowers of this plant; the colors shown being as nearly true as it is reasonably possible to obtain by conventional commercial photographic procedures.

DESCRIPTION OF THE NEW PLANT

The following is a detailed description of my new carnation plant based upon observations of greenhouse grown plants made at Wheat Ridge, Col., in April 1983, the color designations being according to the R.H.S. Colour Chart of The Royal Horticultural Society of London, England.

THE PLANT

Origin: Seedling.

Parentage: Unknown, this seedling being hybridized by crossing selected unidentified plants from breeding stock.

Classification:

*Botanic.*—Hybrid Dianthus Caryophyllus.

*Commercial.*—Greenhouse carnation for cut flower production.

Form: Bush, with tall spray-type shape.

Height: About one meter.

Growth rate: Fast.

Growth habit: Vigorous upright and with strong stem character.

Branching character: Alternate.

Foliage:

*Quantity.*—Abundant.

*Nature of leaf.*—About 75 mm. in length, sessile, and having irregularly crenated margins.

*Texture.*—Leathery.

*Color.*—Upper Side — Blue Green. Under Side — Blue Green.

*Leaflets.*—None.

THE BUD

Size: Medium.

*Diameter.*—About 15 mm.

*Length.*—About 30 mm.

Form: Pear shaped at beginning and becoming generally cylindrical before opening.

Opening rate: Average.

Color of petals:

*When sepals first divide.*—Peach Pink.

*When petals begin to unfurl.*—Peach.

Sepals: Hooded over bud before opening. When flowers open, sepals stand up.

Calyx:

*Shape.*—Funnel shape and long.

*Splitting.*—Calyx does not split.

*Aspect.*—Smooth.

Peduncle or flower stem:

*Length.*—Varies from 10 to 20 cm.

*General character.*—Rigid and erect.

*Color.*—Dark Green.

THE FLOWER

Blooming habit: Profusely and continuously.

Size of bloom: Medium.

*Diameter.*—About 5 cm.

*Depth.*—About 2½ cm.

Borne: Raceme with more than three flowers per stem.
Shape:
*When bloom first opens.*—Flat.
*When bloom matures.*—Flattened convex.
Petalage:
*Number of Petals.*—Thirty-three.
*Arrangement.*—Imbricated.
*Form.*—Fan shaped with deeply crenated apex margin.
*Texture.*—Soft.
*Appearance.*—Velvety.
*Color.*—Outer Petals: Body — 29C fading to about 26D at the tip and occasionally having Red stripes about 6 mm. long in the tip end margin. Base End of Petal — Light Green. Reverse Side — Same as body. Inside Petals: Same as the outer petals but with less Red striping. Reverse Side — Same as body.
*Claw length.*—About 26 mm.
Peduncle or flower stem:
*Length.*—Medium.
*Character.*—Upright with good strength.
*Color.*—Blue Green.
Persistence: Flowers hang on and dry.

Fragrance: Weak.
Lasting quality: As a cut flower — Very good.

REPRODUCTIVE ORGANS

Stamens:
*Number.*—Four, evenly arranged around pistils.
*Anthers.*—Size: About 4 mm. Color: Straw Yellow.
*Filaments.*—Length: About 28 mm. Color: White.
*Pollen.*—Color — Yellow.
Pistils:
*Number.*—Two.
*Styles.*—Length — About 31 mm. Color — White.
*Stigmas.*—Color — White.
Characteristics of ovaries: Diamond shaped with Green top and White bottom.

I claim:

1. The new and distinct variety of carnation, substantially as herein shown and described, characterized by its profuse and continuous production of very light peach colored blooms, and by its vigorous and strong growth habit producing stong main stems about one meter in length and strong flower stems of medium length.

* * * * *

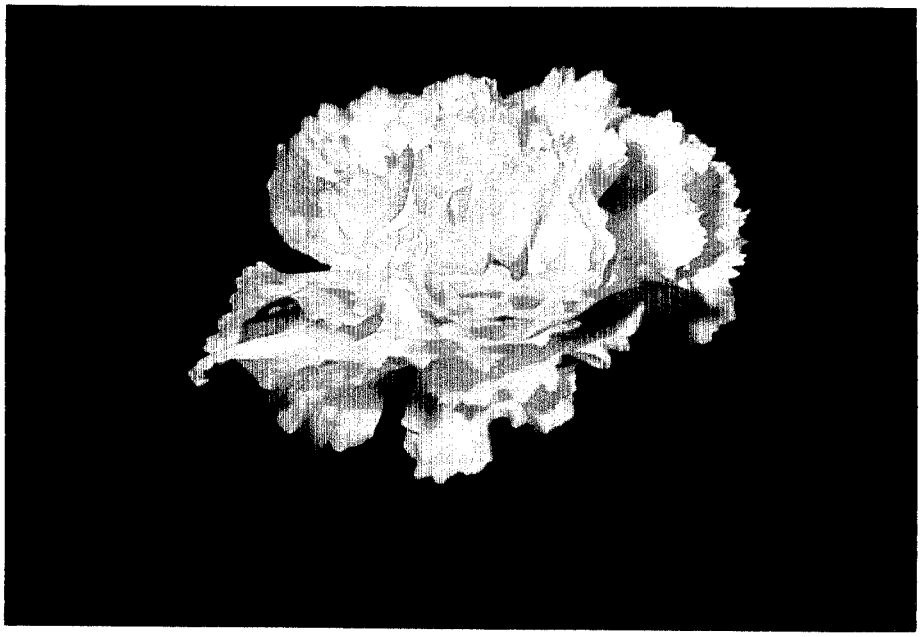
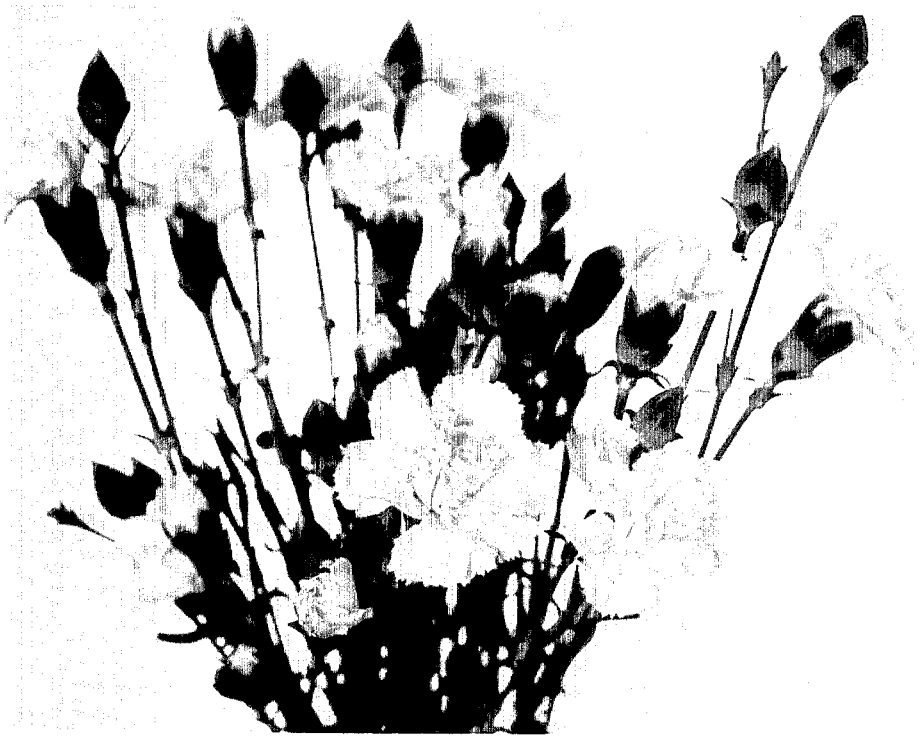

UNITED STATES PATENT AND TRADEMARK OFFICE

CERTIFICATE OF CORRECTION

PATENT NO. : Plant 5,464

DATED : May 7, 1985

INVENTOR(S) : J. F. Sarneel

It is certified that error appears in the above-identified patent and that said Letters Patent are hereby corrected as shown below:

On the title page Assignee should read

-- Assignee: M. Lek en Zonen, B. V.
Nieuwveen, Netherlands --.

Signed and Sealed this

*Twenty-ninth* Day of *October 1985*

[SEAL]

*Attest:*

DONALD J. QUIGG

*Attesting Officer*

*Commissioner of Patents and Trademarks—Designate*